United States Patent [19]
Hu et al.

[11] Patent Number: 5,817,485
[45] Date of Patent: Oct. 6, 1998

[54] NUCLEIC ACIDS AND CELLS FOR RECOMBINANT PRODUCTION OF FIBROBLAST GROWTH FACTOR-10

[75] Inventors: Jing-Shan Hu, Gaithersburg; Jeannine D. Gocayne, Silver Spring, both of Md.

[73] Assignee: Human Genome Sciences, Inc., Rockville, Md.

[21] Appl. No.: 207,412

[22] Filed: Mar. 8, 1994

[51] Int. Cl.⁶ .............................. C12N 15/16; C07K 14/50
[52] U.S. Cl. ................... 435/69.4; 536/23.51; 536/23.5; 435/320.1; 435/325; 435/352.3; 435/254.11; 435/69.1
[58] Field of Search .......................... 530/399; 536/23.5, 536/23.51, 24.31; 435/69.4, 320.1, 252.3, 240.2, 254.4, 325, 69.1

[56] References Cited

U.S. PATENT DOCUMENTS

| | | | |
|---|---|---|---|
| 4,868,113 | 9/1989 | Jaye et al. | 435/69.4 |
| 5,155,214 | 10/1992 | Baird et al. | 514/381 |

FOREIGN PATENT DOCUMENTS

| | | | |
|---|---|---|---|
| 0510662A1 | 10/1992 | European Pat. Off. | C07K 13/00 |
| WO 94/03199 | 2/1994 | WIPO . | |

OTHER PUBLICATIONS

Burgess, W.H. and Maciag, T., The Heparin–Binding (Fi8roblast Growth Factor Family of Proteins, Annv. Rev. Biochem., 58:575–606 (1989).
Basilico, C. and Moscatelli, D., The FGF Family of Growth Factors and Oncogenes, Adv. in Cancer Res., 59:115–165 (1992).
Jaye et al. *Science* 233:541–545 (1986).
Aaronson et al *Ann NY Acad Sci* 638: 62–77 (1991).
Barinager *Sciences* 264: 772–774 (1994).
Basilico et al *Adv Caancer Res* 59: 115–162 (1992).
Adams, M.D. et al. (1993) Gen Bank database record, Acc. No. T09003.
Adams, M.D. et al. (1993) *Nature genetics* 4: 373–80.

*Primary Examiner*—David L. Fitzgerald
*Attorney, Agent, or Firm*—Elliot Olstein; J. G. Mullins

[57] ABSTRACT

Disclosed is a human FGF-10 polypeptide and DNA(RNA) encoding such FGF-10 polypeptide. Also provided is a procedure for producing such polypeptide by recombinant techniques and antibodies and antagonist/inhibitors against such polypeptide. Such polypeptides may be combined with a suitable pharmaceutical carrier or diluent to provide diagnostic, therapeutic and/or prophylactic effects against various diseases. There is also disclosed methods of utilizing antibodies and antagonists against such polypeptide for therapeutic purposes.

49 Claims, 9 Drawing Sheets

FIG. 1A

```
1   GGCACGAGCGGAGGACAGCTCCTGCCTGCNGCTTCCAGACCCAGGAAGCCTGAGGGAAG   60
    -----+---------+---------+---------+---------+---------+
    A R A E D S S C L ? L P D D P G S L R G R

61  GAAGGAAGTACGGGCGAAATCATCAGATTGGCTTCCCAGATTTGGGAATCTGAAGCGGGC  120
    -----+---------+---------+---------+---------+---------+
    K E V R A K S S D W L P R F G N L K R A

121 CCACATCTTCCGGCCAACTTCCATTGAACTTCCCAGCACTCGAAAGAGGACCGAAATGGA  180
    -----+---------+---------+---------+---------+---------+
    H I F R P T S I E L P S T R K R T E M E

181 GAGCAAAGAACCCCAGCTCAAAGGGATTGTGACAAGGTTATTCAGCCAGCAGGGATACTT  240
    -----+---------+---------+---------+---------+---------+
    S K E P Q L K G I V T R L F S Q Q G Y F

241 CCTGCAGATGCACCCAGATGGTACCATTGATGGGACCAAGGACGAAAACAGCGACTACAC  300
    -----+---------+---------+---------+---------+---------+
    L Q M H P D G T I D G T K D E N S D Y T

301 TCTCTTCAATCTAATTCCCGTGGGCCTGCGTGTAGTGGCCATCCAAGGAGTGAAGGCTAG  360
    -----+---------+---------+---------+---------+---------+
    L F N L I P V G L R V V A I Q G V K A S
```

FIG. 1B

```
361  CCTCTATGTGGCCATGAATGGTGAAGGCTATCTCTACAGTTCAGATGTTTCACTCCAGA  420
      ---------+---------+---------+---------+---------+---------+
      L  Y  V  A  M  N  G  E  G  Y  L  Y  S  S  D  V  F  T  P  E

421  ATGCAAATTCAAGGATCTGGTGTGTTTGAAAACTACTATGTGATCTATTCTTCCACACTGTA  480
      ---------+---------+---------+---------+---------+---------+
      C  K  F  K  D  L  V  F  E  N  Y  Y  V  I  Y  S  S  T  L  Y

481  CCGCCAGCAAGAATCAGGCCGAGCTTGGTTTCTGGGACTCAATAAAGAAGGTCAAATTAT  540
      ---------+---------+---------+---------+---------+---------+
      R  Q  Q  E  S  G  R  A  W  F  L  G  L  N  K  E  G  Q  I  M

541  GAAGGGGAACAGAGTGAAGAAAAAACCAAGCCCTCATCACATTTGTACCGAAACCTATTGA  600
      ---------+---------+---------+---------+---------+---------+
      K  G  N  R  V  K  K  T  K  P  S  S  H  F  V  P  K  P  I  E

601  AGTGTGTATGTACAGAGAACCATCGCTACATGAAATTGGAGAAAACAAGGGCGTTCAAG  660
      ---------+---------+---------+---------+---------+---------+
      V  C  M  Y  R  E  P  S  L  H  E  I  G  E  K  Q  G  R  S  R

661  GAAAAGTTCTGGAACACCAACCATGAATGGAGGCAAAGTTGTGAATCAAGATTCAACATA  720
      ---------+---------+---------+---------+---------+---------+
      K  S  S  G  T  P  T  M  N  G  G  K  V  V  N  Q  D  S  T  *
```

FIG. 1C

```
721  GCTTGAGANCTCTCCCCTTCTCCTCCTCCCCTTCCTCATCCCCTCCCCTTNCCTTNCTTCCCATTT
     ----------+---------+---------+---------+---------+---------+ 780
781  ACCCTTNCTTNCAGTAAATCNCCCCAGGNGNGGAAATAAATTGCCAACGGNAGGCNTAG
     ----------+---------+---------+---------+---------+---------+ 840
841  TGGTTAGNTTTTGACTCAAAATNTTCTTTGTGTGGGCAAGGAATTNACCAGGTTGTTTTT
     ----------+---------+---------+---------+---------+---------+ 900
901  CATGTGGTGGAATTCCGNGCCAAGTTGGCNTTAAGGAGGNATATCGGTGGG
     ----------+---------+---------+---------+--------- 951
961  AATTCACGTTCACAAAGATTATCACACTTAAAAGCAAAGGAAAAATAAATCAGAACTCC
     ----------+---------+---------+---------+---------+---------+ 1020
1021 ATAAATATTAAACTAAACTGTATTGTTATTAGTAGAAGGCTAATTGTAATGAAGACATTA
     ----------+---------+---------+---------+---------+---------+ 1080
1081 ATAAAGGTGAAATAAACTTAAAAAAAAAAAAAAAAAAAA
     ----------+---------+---------+-------- 1121
```

FIG. 2A

```
        1                                                                            50
Fgf-1   ..........  ..........  ..........  ..........  ..........
Fgf-2   ..........  ..........  ..........  .LGDRGRGR   ALPGGRLGGR  ..........
Fgf-4   ..........  MS.GPGTAAV  ALLPAVLLAL  LA........  ..........  GRGRAPERVG
Fgf-6   MALGQKLFIT  MSRGAGRLQG  TLWALVFLGI  LV........  ..........  .PWAGRGGAA
Fgf-5   ..........  ..MSL       SFLLLLFFSH  LILSAWAHGE  KRLAPKGQPG  .GMVPSPAG
Fgf-10  ..........  ..........  ..........  ..NSARAEDS  SCLXLPDGS
Fgf-9   ..........  ..........  ..........  ..MAPLGEVG  NYFGVQDAVP
Fgf-3   ..........  ..........  ..........  ..........  ..MGLIW
Fgf-7   ..........  ..........  ..........  ..........  MHKWILTWIL 51                                                                           100
Fgf-1   ..........  ..........  ..........  .....MAE    GEITTFTALT  EKFN...LPP
Fgf-2   GRGRGRGTAA  PRAAPAARGS  RPGPAGTMAA   GSITTLPALP  EDGGSGAFPP
Fgf-4   APTAPNGTLE  AELERRWESL  VALSLARLPV   AA..QPKEAA  VQSGAGDYLL
Fgf-6   TR.ANNTLLD  S...RGWGTL  LSRSRAGLAG   EI.....AG   VNWESG.YLV
Fgf-5   PAATDRNPIG  SSSRQSSSSA  MSSSSASSSP   AASLGSQGSG  LEQSSFQWSP
Fgf-10  LRGRKEVRAK  SSDWLPRFGN  LKRAHIFRPT   SIELPSTRKR  TEMESKEPQL
Fgf-9   FGNVPVLPVD  SPVLLS....  ...DHLGQSE   AGGLPRGPAV  TDLD...HL
Fgf-3   LLLL......  ........SL  LEPGWPAAGP   GARLRRDAGG  RGG.VYEHL.
Fgf-7   PTLLYRSCFH  IICLVGTISL  ACNDMTPEQM   ATNVNCSSPE  RHTRSYDYME
```

FIG. 2B

```
        101                                                                    150
Fgf-1   GNYKKPKLLY  CSNG.GHFLR  ILPDGTVDGT  RDRSDQHIQL  QLSAESVGEV
Fgf-2   GHFKDPKRLY  CKNG.GFFLR  IHPDGRVDGV  REKSDPHIKL  QLQAEERGVV
Fgf-4   .GIKRLRRLY  CNVGIGFHLQ  ALPDGRIGGA  HADT.RDSLL  ELSPVERGVV
Fgf-6   .GIKRQRRLY  CNVGIGFHLQ  VLPDGRISGT  HEEN.PYSLL  EISTVERGVV
Fgf-5   .SGRRTGSLY  CRVGIGFHLQ  IYPDGKVNGS  HEAN.MLSVL  EIFAVSQGIV
Fgf-10  KGIVTR..LF  SQQ..GYFLQ  MHPDGTIDGT  KDENSDYTLF  NLIPVGLRVV
Fgf-9   KGILRRRQLY  CRT..GFHLE  IFPNGTIQGT  RKDHSRFGIL  EFISIAVGLV
Fgf-3   GGAPRRRKLY  CAT..KYHLQ  LHPSGRVNGS  LE.NSAYSIL  EITAVEVGIV
Fgf-7   GGDIRVRRLF  CRT..QWYLR  IDKRGKVKGT  QEMKNNYNIM  EIRTVAVGIV 151                                                                    200
Fgf-1   YIKSTETGQY  LAMDTDGLLY  GSQTPNEECL  FLERLEENHY  NTYISKKH..
Fgf-2   SIKGVCANRY  LAMKEDGRLL  ASKCVTDECF  FFERLESNNY  NTYRSRKY..
Fgf-4   SIFGVASRFF  VAMSSKGKLY  GSPFFTDECT  FKEILLPNNY  NAYESYKY..
Fgf-6   SLFGVRSALF  VAMNSKGRLY  ATPSFQEECK  FRETLLPNNY  NAYESDLY..
Fgf-5   GIRGVFSNKF  LAMSKKGKLH  ASAKFTDDCK  FRERFQENSY  NTYASAIH..
Fgf-10  AIQGVKASLY  VAMNGEGYLY  SSDVFTPECK  FKDLVFENYY  VIYSSTLY..
Fgf-9   SIRGVDSGLY  LGMNEKGELY  GSEKLTQECV  FREQFEENWY  NTYSSNLY..
Fgf-3   AIRGLFSGRY  LAMNKRGRLY  ASEHYSAECE  FVERIHELGY  NTYASRLYRT
Fgf-7   AIKGVESEFY  LAMNKEGKLY  AKKECNEDCN  FKELILENHY  NTYAS.....
```

FIG. 2C

```
        151                                                           200
Fgf-1   ..........  YIKSTETGQY  LAMDTDGLLY  GSQTPNEECL  FLERLEENHY  NTYISKKH..
Fgf-2   ..........  SIKGVCANRY  LAMKEDGRLL  ASKCVTDECF  FFERLESNNY  NTYRSRKY..
Fgf-4   ..........  SIFGVASRFF  VAMSSKGKLY  GSPFFTDECT  FKEILLPNNY  NAYESYKY..
Fgf-6   ..........  SLFGVRSALF  VAMNSKGRLY  ATPSFQEECK  FRETLLPNNY  NAYESDLY..
Fgf-5   ..........  GIRGVFSNKF  LAMSKKGKLH  ASAKFTDDCK  FRERFQENSY  NTYASAIH..
Fgf-10  ..........  AIQGVKASLY  VAMNGEGYLY  SSDVFTPECK  FKDLVFENYY  VIYSSTLY..
Fgf-9   ..........  SIRGVDSGLY  LGMNEKGELY  GSEKLTQECV  FREQFEENWY  NTYSSNLY..
Fgf-3   ..........  AIRGLFSGRY  LAMNKRGRLY  ASEHYSAECE  FVERIHELGY  NTYASRLYRT
Fgf-7   ..........  AIKGVESEFY  LAMNKEGKLY  AKKECNEDCN  FKELILENHY  NTYAS.....
                                               *         *    *

201                                                           250
Fgf-1   ..AEKNWFVG  LKKNGSCKRG  ..PRTHYGQK  AILFLPLPVS
Fgf-2   ..T..SWYVA  LKRTGQYKLG  ..SKTGPGQK  AILFLPMSAK
Fgf-4   .PG M.....  .FIA......  YIA........  LSKYGRVKRG  NRVSPTMK  VTHFLPRL..
Fgf-6   .QG T.....  .YIA......                ..SKVSPIMT  VTHFLPRI..
Fgf-5   ..RT EKTGREWYVA  LNKRGKAKRG  CSPRVKPQHI  STHFLPRFKQ
Fgf-10  ..RQ QESGRAWFLG  LNKEGQIMKG  ..NRVKKTKP  SSHFVPKPIE
Fgf-9   ..KH VDTGRRYYVA  LNKDGTPREG  ..TRTKRHQK  FTHFLPRPVD
Fgf-3   VSSTPGARRQ  PSAERLWYVS  VNGKGRPRRG  ..FKTRRTQK  SSLFLPRVLD
Fgf-7   ..AKWT HNGGEM.FVA  LNQKGIPVRG  ..KKTKKEQK  TAHFLPMAIT
```

FIG. 2D

```
         251                                                                       300
Fgf-1    SD..........  ............ ............ ............ ............ ......
Fgf-2    S...........  ............ ............ ............ ............ ......
Fgf-4    ............  ............ ............ ............ ............ ......
Fgf-6    ............  ............ ............ ............ ............ ......
Fgf-5    SEQPELSFTV    TVPEKKNPPS   PIKSKIPLSA   PRKNTNSVKY   RLKFRFG...   ......
Fgf-10   VCMYREPSLH    EIGEKQGRSR   KSSGTPTMNG   GKVVNQDST*   ............ ......
Fgf-9    PDKVPELYKD    ILSQS.....   ............ ............ ............ ......
Fgf-3    HRDHEMVRQL    QSGLPRPPGK   ............ ............ ............ ......
Fgf-7    ............  ............ QSPDNLEPSH   VQASRLGSQL   ............ ......

301
Fgf-1    ......
Fgf-2    ......
Fgf-4    ......
Fgf-6    ......
Fgf-5    ......
Fgf-10   ......
Fgf-9    ......
Fgf-3    EASAH.
Fgf-7    ......
```

1. Heart
2. Brain
3. Placenta
4. Lung
5. Liver
6. Skeletal muscle
7. Kidney
8. Pancrease Lane 1: FGF-10
Lane 2: control
Lane 3: no DNA/RNA

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
      ( A ) LENGTH: 1121 base pairs
      ( B ) TYPE: nucleic acid
      ( C ) STRANDEDNESS: single
      ( D ) TOPOLOGY: linear ( i i ) MOLECULE TYPE: DNA (genomic)

( i x ) FEATURE:
      ( A ) NAME/KEY: CDS
      ( B ) LOCATION: 210..752

( x i ) SEQUENCE DESCRIPTION: SEQ ID NO:1:

```
GGCAAAGTGG GATGATCTGT CACTACACCT GCAGCACCAC GCTCGGAGGA CAGCTCCTGC      60

CTGCAGCTTC CAGACCCAGG AAGCCTGAGG GGAAGGAAGG AAGTACGGGC GAAATCATCA     120

GATTGGCTTC CCAGATTTGG GAATCTGAAG CGGGCCCACA TCTTCCGGCC AACTTCCATT     180

GAACTTCCCA GCACTCGAAA GGGACCGAA ATG GAG AGC AAA GAA CCC CAG CTC      233
                                 Met Glu Ser Lys Glu Pro Gln Leu
                                  1               5

AAA GGG ATT GTG ACA AGG TTA TTC AGC CAG CAG GGA TAC TTC CTG CAG      281
Lys Gly Ile Val Thr Arg Leu Phe Ser Gln Gln Gly Tyr Phe Leu Gln
         10                  15                  20

ATG CAC CCA GAT GGT ACC ATT GAT GGG ACC AAG GAC GAA AAC AGC GAC      329
Met His Pro Asp Gly Thr Ile Asp Gly Thr Lys Asp Glu Asn Ser Asp
 25                  30                  35                  40

TAC ACT CTC TTC AAT CTA ATT CCC GTG GGC CTG CGT GTA GTG GCC ATC      377
Tyr Thr Leu Phe Asn Leu Ile Pro Val Gly Leu Arg Val Val Ala Ile
                     45                  50                  55

CAA GGA GTG AAG GCT AGC CTC TAT GTG GCC ATG AAT GGT GAA GGC TAT      425
Gln Gly Val Lys Ala Ser Leu Tyr Val Ala Met Asn Gly Glu Gly Tyr
             60                  65                  70

CTC TAC AGT TCA GAT GTT TTC ACT CCA GAA TGC AAA TTC AAG GAA TCT      473
Leu Tyr Ser Ser Asp Val Phe Thr Pro Glu Cys Lys Phe Lys Glu Ser
         75                  80                  85

GTG TTT GAA AAC TAC TAT GTG ATC TAT TCT TCC ACA CTG TAC CGC CAG      521
Val Phe Glu Asn Tyr Tyr Val Ile Tyr Ser Ser Thr Leu Tyr Arg Gln
     90                  95                 100

CAA GAA TCA GGC CGA GCT TGG TTT CTG GGA CTC AAT AAA GAA GGT CAA      569
Gln Glu Ser Gly Arg Ala Trp Phe Leu Gly Leu Asn Lys Glu Gly Gln
105                 110                 115                 120

ATT ATG AAG GGG AAC AGA GTG AAG AAA ACC AAG CCC TCA TCA CAT TTT      617
Ile Met Lys Gly Asn Arg Val Lys Lys Thr Lys Pro Ser Ser His Phe
                125                 130                 135

GTA CCG AAA CCT ATT GAA GTG TGT ATG TAC AGA GAA CCA TCG CTA CAT      665
Val Pro Lys Pro Ile Glu Val Cys Met Tyr Arg Glu Pro Ser Leu His
            140                 145                 150

GAA ATT GGA GAA AAA CAA GGG CGT TCA AGG AAA AGT TCT GGA ACA CCA      713
Glu Ile Gly Glu Lys Gln Gly Arg Ser Arg Lys Ser Ser Gly Thr Pro
        155                 160                 165

ACC ATG AAT GGA GGC AAA GTT GTG AAT CAA GAT TCA ACA TAGCTGAGAA      762
Thr Met Asn Gly Gly Lys Val Val Asn Gln Asp Ser Thr
    170                 175                 180

CTCTCCCCTT CTTCCCTCTC TCATCCCTTC CCCTTCCCTT CCTTCCCATT TACCCATTTC    822
```

```
CTTCCAGTAA ATCCACCCAA GGAGAGGAAA ATAAAATGAC AACGCAAGCA CCTAGTGGCT        882

AAGATTCTGC ACTCAAAATC TTCCTTTGTG TAGGACAAGA AAATTGAACC AAAGCTTGCT        942

TGTTGCAATG TTGTAGAAAA TTCACGTTCA CAAAGATTAT CACACTTAAA AGCAAAGGAA       1002

AAAATAAATC AGAACTCCAT AAATATTAAA CTAAACTGTA TTGTTATTAG TAGAAGGCTA       1062

ATTGTAATGA AGACATTAAT AAAGGTGAAA TAAACTTAAA AAAAAAAAA AAAAAAAA         1121
```

( 2 ) INFORMATION FOR SEQ ID NO:2:

( i ) SEQUENCE CHARACTERISTICS:
        ( A ) LENGTH: 181 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Glu Ser Lys Glu Pro Gln Leu Lys Gly Ile Val Thr Arg Leu Phe
 1               5                  10                  15

Ser Gln Gln Gly Tyr Phe Leu Gln Met His Pro Asp Gly Thr Ile Asp
            20                  25                  30

Gly Thr Lys Asp Glu Asn Ser Asp Tyr Thr Leu Phe Asn Leu Ile Pro
        35                  40                  45

Val Gly Leu Arg Val Val Ala Ile Gln Gly Val Lys Ala Ser Leu Tyr
    50                  55                  60

Val Ala Met Asn Gly Glu Gly Tyr Leu Tyr Ser Ser Asp Val Phe Thr
65                  70                  75                  80

Pro Glu Cys Lys Phe Lys Glu Ser Val Phe Glu Asn Tyr Tyr Val Ile
                85                  90                  95

Tyr Ser Ser Thr Leu Tyr Arg Gln Gln Glu Ser Gly Arg Ala Trp Phe
               100                 105                 110

Leu Gly Leu Asn Lys Glu Gly Gln Ile Met Lys Gly Asn Arg Val Lys
           115                 120                 125

Lys Thr Lys Pro Ser Ser His Phe Val Pro Lys Pro Ile Glu Val Cys
       130                 135                 140

Met Tyr Arg Glu Pro Ser Leu His Glu Ile Gly Glu Lys Gln Gly Arg
145                 150                 155                 160

Ser Arg Lys Ser Ser Gly Thr Pro Thr Met Asn Gly Gly Lys Val Val
                165                 170                 175

Asn Gln Asp Ser Thr
            180
```

( 2 ) INFORMATION FOR SEQ ID NO:3:

( i ) SEQUENCE CHARACTERISTICS:
        ( A ) LENGTH: 17 AMINO ACIDS
        ( B ) TYPE: AMINO ACID
        ( C ) STRANDEDNESS:
        ( D ) TOPOLOGY: LINEAR ( i i ) MOLECULE TYPE: PROTEIN ( x i ) SEQUENCE DESCRIPTION: SEQ ID NO:3:

```
Gly Xaa Leu Xaa Xaa Xaa Xaa Xaa Xaa Xaa Xaa Xaa Cys Xaa Phe
                5                   10                  15

Xaa Glu
```

( 2 ) INFORMATION FOR SEQ ID NO:4:

( i ) SEQUENCE CHARACTERISTICS:

( A ) LENGTH: 18 BASE PAIRS
        ( B ) TYPE: NUCLEIC ACID
        ( C ) STRANDEDNESS: SINGLE
        ( D ) TOPOLOGY: LINEAR ( i i ) MOLECULE TYPE: Oligonucleotide ( x i ) SEQUENCE DESCRIPTION: SEQ ID NO:4:

ATGCTTCCGG CTCGTATG                                                                                  18

( 2 ) INFORMATION FOR SEQ ID NO:5:

( i ) SEQUENCE CHARACTERISTICS:
        ( A ) LENGTH: 19 BASE PAIRS
        ( B ) TYPE: NUCLEIC ACID
        ( C ) STRANDEDNESS: SINGLE
        ( D ) TOPOLOGY: LINEAR ( i i ) MOLECULE TYPE: Oligonucleotide ( x i ) SEQUENCE DESCRIPTION: SEQ ID NO:5:

GGGTTTTCCC AGTCACGAC                                                                                 19

( 2 ) INFORMATION FOR SEQ ID NO:6:

( i ) SEQUENCE CHARACTERISTICS:
        ( A ) LENGTH: 24 BASE PAIRS
        ( B ) TYPE: NUCLEIC ACID
        ( C ) STRANDEDNESS: SINGLE
        ( D ) TOPOLOGY: LINEAR ( i i ) MOLECULE TYPE: Oligonucleotide ( x i ) SEQUENCE DESCRIPTION: SEQ ID NO:6:

GTGAGATCTG AGGGAAGAAG GGGA                                                                           24

( 2 ) INFORMATION FOR SEQ ID NO:7:

( i ) SEQUENCE CHARACTERISTICS:
        ( A ) LENGTH: 18 BASE PAIRS
        ( B ) TYPE: NUCLEIC ACID
        ( C ) STRANDEDNESS: SINGLE
        ( D ) TOPOLOGY: LINEAR ( i i ) MOLECULE TYPE: Oligonucleotide ( x i ) SEQUENCE DESCRIPTION: SEQ ID NO:7:

CCACCGATAA TCCTCCTT                                                                                  18

( 2 ) INFORMATION FOR SEQ ID NO:8:

( i ) SEQUENCE CHARACTERISTICS:
        ( A ) LENGTH: 155 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:8:

Met  Ala  Glu  Gly  Glu  Ile  Thr  Thr  Phe  Thr  Ala  Leu  Thr  Glu  Lys  Phe
        1              5                        10                       15

Asn  Leu  Pro  Pro  Gly  Asn  Tyr  Lys  Lys  Pro  Lys  Leu  Leu  Tyr  Cys  Ser
                       20                       25                       30

Asn  Gly  Gly  His  Phe  Leu  Arg  Ile  Leu  Pro  Asp  Gly  Thr  Val  Asp  Gly
                            35                       40                       45

Thr  Arg  Asp  Arg  Ser  Asp  Gln  His  Ile  Gln  Leu  Gln  Leu  Ser  Ala  Glu
                  50                       55                       60

```
Ser  Val  Gly  Glu  Val  Tyr  Ile  Lys  Ser  Thr  Glu  Thr  Gly  Gln  Tyr  Leu
65                  70                       75                            80

Ala  Met  Asp  Thr  Asp  Gly  Leu  Leu  Tyr  Gly  Ser  Gln  Thr  Pro  Asn  Glu
               85                       90                       95

Glu  Cys  Leu  Phe  Leu  Glu  Arg  Leu  Glu  Glu  Asn  His  Tyr  Asn  Thr  Tyr
               100                      105                      110

Ile  Ser  Lys  Lys  His  Ala  Glu  Lys  Asn  Trp  Phe  Val  Gly  Leu  Lys  Lys
          115                      120                      125

Asn  Gly  Ser  Cys  Lys  Arg  Gly  Pro  Arg  Thr  His  Tyr  Gly  Gln  Lys  Ala
     130                      135                 140

Ile  Leu  Phe  Leu  Pro  Leu  Pro  Val  Ser  Ser  Asp
145                 150                      155
```

(2) INFORMATION FOR SEQ ID NO:9:

(i) SEQUENCE CHARACTERISTICS:
      (A) LENGTH: 210 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:9:

```
Leu  Gly  Asp  Arg  Gly  Arg  Gly  Arg  Ala  Leu  Pro  Gly  Gly  Arg  Leu  Gly
1                   5                        10                      15

Gly  Arg  Gly  Arg  Gly  Arg  Ala  Pro  Glu  Arg  Val  Gly  Gly  Arg  Gly  Arg
               20                       25                       30

Gly  Arg  Gly  Thr  Ala  Ala  Pro  Arg  Ala  Ala  Pro  Ala  Ala  Arg  Gly  Ser
               35                       40                       45

Arg  Pro  Gly  Pro  Ala  Gly  Thr  Met  Ala  Ala  Gly  Ser  Ile  Thr  Thr  Leu
     50                       55                       60

Pro  Ala  Leu  Pro  Glu  Asp  Gly  Gly  Ser  Gly  Ala  Phe  Pro  Pro  Gly  His
65                  70                       75                            80

Phe  Lys  Asp  Pro  Lys  Arg  Leu  Tyr  Cys  Lys  Asn  Gly  Gly  Phe  Phe  Leu
               85                       90                       95

Arg  Ile  His  Pro  Asp  Gly  Arg  Val  Asp  Gly  Val  Arg  Glu  Lys  Ser  Asp
               100                      105                      110

Pro  His  Ile  Lys  Leu  Gln  Leu  Gln  Ala  Glu  Glu  Arg  Gly  Val  Val  Ser
          115                      120                      125

Ile  Lys  Gly  Val  Cys  Ala  Asn  Arg  Tyr  Leu  Ala  Met  Lys  Glu  Asp  Gly
     130                      135                      140

Arg  Leu  Leu  Ala  Ser  Lys  Cys  Val  Thr  Asp  Glu  Cys  Phe  Phe  Phe  Glu
145                 150                      155                           160

Arg  Leu  Glu  Ser  Asn  Asn  Tyr  Asn  Thr  Tyr  Arg  Ser  Arg  Lys  Tyr  Thr
                    165                      170                      175

Ser  Trp  Tyr  Val  Ala  Leu  Lys  Arg  Thr  Gly  Gln  Tyr  Lys  Leu  Gly  Ser
               180                      185                      190

Lys  Thr  Gly  Pro  Gly  Gln  Lys  Ala  Ile  Leu  Phe  Leu  Pro  Met  Ser  Ala
          195                      200                      205

Lys  Ser
210
```

(2) INFORMATION FOR SEQ ID NO:10:

(i) SEQUENCE CHARACTERISTICS:
      (A) LENGTH: 206 amino acids
      (B) TYPE: amino acid (C) STRANDEDNESS: single
(D) TOPOLOGY: linear (i i) MOLECULE TYPE: protein (x i) SEQUENCE DESCRIPTION: SEQ ID NO:10:

| Met 1 | Ser | Gly | Pro | Gly 5 | Thr | Ala | Ala | Val | Ala 10 | Leu | Leu | Pro | Ala | Val 15 | Leu |
|---|---|---|---|---|---|---|---|---|---|---|---|---|---|---|---|
| Leu | Ala | Leu | Leu 20 | Ala | Pro | Trp | Ala | Gly 25 | Arg | Gly | Gly | Ala | Ala 30 | Ala | Pro |
| Thr | Ala | Pro 35 | Asn | Gly | Thr | Leu | Glu 40 | Ala | Glu | Leu | Glu | Arg 45 | Arg | Trp | Glu |
| Ser | Leu 50 | Val | Ala | Leu | Ser | Leu 55 | Ala | Arg | Leu | Pro | Val 60 | Ala | Ala | Gln | Pro |
| Lys 65 | Glu | Ala | Ala | Val | Gln 70 | Ser | Gly | Ala | Gly | Asp 75 | Tyr | Leu | Leu | Gly | Ile 80 |
| Lys | Arg | Leu | Arg | Arg 85 | Leu | Tyr | Cys | Asn | Val 90 | Gly | Ile | Gly | Phe | His 95 | Leu |
| Gln | Ala | Leu | Pro 100 | Asp | Gly | Arg | Ile | Gly 105 | Gly | Ala | His | Ala | Asp 110 | Thr | Arg |
| Asp | Ser | Leu 115 | Leu | Glu | Leu | Ser | Pro 120 | Val | Glu | Arg | Gly | Val 125 | Val | Ser | Ile |
| Phe | Gly 130 | Val | Ala | Ser | Arg | Phe 135 | Phe | Val | Ala | Met | Ser 140 | Ser | Lys | Gly | Lys |
| Leu 145 | Tyr | Gly | Ser | Pro | Phe 150 | Phe | Thr | Asp | Glu | Cys 155 | Thr | Phe | Lys | Glu | Ile 160 |
| Leu | Leu | Pro | Asn | Asn 165 | Tyr | Asn | Ala | Tyr | Glu 170 | Ser | Tyr | Lys | Tyr | Pro 175 | Gly |
| Met | Phe | Ile | Ala 180 | Leu | Ser | Lys | Asn | Gly 185 | Lys | Thr | Lys | Lys 190 | Gly | Asn | Arg |
| Val | Ser | Pro 195 | Thr | Met | Lys | Val | Thr 200 | His | Phe | Leu | Pro | Arg 205 | Leu | | |

(2) INFORMATION FOR SEQ ID NO:11:

(i) SEQUENCE CHARACTERISTICS:
(A) LENGTH: 208 amino acids
(B) TYPE: amino acid
(C) STRANDEDNESS: single
(D) TOPOLOGY: linear (i i) MOLECULE TYPE: protein (x i) SEQUENCE DESCRIPTION: SEQ ID NO:11:

| Met 1 | Ala | Leu | Gly | Gln 5 | Lys | Leu | Phe | Ile | Thr 10 | Met | Ser | Arg | Gly | Ala 15 | Gly |
|---|---|---|---|---|---|---|---|---|---|---|---|---|---|---|---|
| Arg | Leu | Gln | Gly 20 | Thr | Leu | Trp | Ala | Leu 25 | Val | Phe | Leu | Gly | Ile 30 | Leu | Val |
| Gly | Met | Val 35 | Val | Pro | Ser | Pro | Ala 40 | Gly | Thr | Arg | Ala | Asn 45 | Asn | Thr | Leu |
| Leu | Asp 50 | Ser | Arg | Gly | Trp | Gly 55 | Thr | Leu | Leu | Ser | Arg 60 | Ser | Arg | Ala | Gly |
| Leu | Ala 65 | Gly | Glu | Ile | Ala | Gly 70 | Val | Asn | Trp | Glu | Ser 75 | Gly | Tyr | Leu | Val 80 |
| Gly | Ile | Lys | Arg | Gln 85 | Arg | Arg | Leu | Tyr | Cys 90 | Asn | Val | Gly | Ile | Gly 95 | Phe |
| His | Leu | Gln | Val 100 | Leu | Pro | Asp | Gly | Arg 105 | Ile | Ser | Gly | Thr | His 110 | Glu | Glu |

|     |     |     |     |     |     |     |     |     |     |     |     |     |     |     |
| --- | --- | --- | --- | --- | --- | --- | --- | --- | --- | --- | --- | --- | --- | --- |
| Asn | Pro | Tyr<br>115 | Ser | Leu | Leu | Glu | Ile | Ser<br>120 | Thr | Val | Glu | Arg<br>125 | Gly | Val | Val |
| Ser | Leu<br>130 | Phe | Gly | Val | Arg | Ser<br>135 | Ala | Leu | Phe | Val | Ala<br>140 | Met | Asn | Ser | Lys |
| Gly<br>145 | Arg | Leu | Tyr | Ala | Thr<br>150 | Pro | Ser | Phe | Gln | Glu<br>155 | Glu | Cys | Lys | Phe | Arg<br>160 |
| Glu | Thr | Leu | Leu | Pro<br>165 | Asn | Asn | Tyr | Asn | Ala<br>170 | Tyr | Glu | Ser | Asp | Leu<br>175 | Tyr |
| Gln | Gly | Thr | Tyr<br>180 | Ile | Ala | Leu | Ser | Lys<br>185 | Tyr | Gly | Arg | Val | Lys<br>190 | Arg | Gly |
| Ser | Lys | Val<br>195 | Ser | Pro | Ile | Met | Thr<br>200 | Val | Thr | His | Phe | Leu<br>205 | Pro | Arg | Ile |

(2) INFORMATION FOR SEQ ID NO:12:

(i) SEQUENCE CHARACTERISTICS:
        (A) LENGTH: 268 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:12:

|     |     |     |     |     |     |     |     |     |     |     |     |     |     |     |
| --- | --- | --- | --- | --- | --- | --- | --- | --- | --- | --- | --- | --- | --- | --- |
| Met<br>1 | Ser | Leu | Ser | Phe<br>5 | Leu | Leu | Leu | Leu | Phe<br>10 | Phe | Ser | His | Leu | Ile | Leu<br>15 |
| Ser | Ala | Trp | Ala<br>20 | His | Gly | Glu | Lys | Arg<br>25 | Leu | Ala | Pro | Lys | Gly<br>30 | Gln | Pro |
| Gly | Pro | Ala<br>35 | Ala | Thr | Asp | Arg | Asn<br>40 | Pro | Ile | Gly | Ser | Ser<br>45 | Ser | Arg | Gln |
| Ser | Ser<br>50 | Ser | Ser | Ala | Met | Ser<br>55 | Ser | Ser | Ser | Ala | Ser<br>60 | Ser | Ser | Pro | Ala |
| Ala<br>65 | Ser | Leu | Gly | Ser | Gln<br>70 | Gly | Ser | Gly | Leu | Glu<br>75 | Gln | Ser | Ser | Phe | Gln<br>80 |
| Trp | Ser | Pro | Ser | Gly<br>85 | Arg | Arg | Thr | Gly | Ser<br>90 | Leu | Tyr | Cys | Arg | Val<br>95 | Gly |
| Ile | Gly | Phe | His<br>100 | Leu | Gln | Ile | Tyr | Pro<br>105 | Asp | Gly | Lys | Val | Asn<br>110 | Gly | Ser |
| His | Glu | Ala<br>115 | Asn | Met | Leu | Ser | Val<br>120 | Leu | Glu | Ile | Phe | Ala<br>125 | Val | Ser | Gln |
| Gly | Ile<br>130 | Val | Gly | Ile | Arg | Gly<br>135 | Val | Phe | Ser | Asn | Lys<br>140 | Phe | Leu | Ala | Met |
| Ser<br>145 | Lys | Lys | Gly | Lys | Leu<br>150 | His | Ala | Ser | Ala | Lys<br>155 | Phe | Thr | Asp | Asp | Cys<br>160 |
| Lys | Phe | Arg | Glu | Arg<br>165 | Phe | Gln | Glu | Asn | Ser<br>170 | Tyr | Asn | Thr | Tyr | Ala<br>175 | Ser |
| Ala | Ile | His | Arg<br>180 | Thr | Glu | Lys | Thr | Gly<br>185 | Arg | Glu | Trp | Tyr | Val<br>190 | Ala | Leu |
| Asn | Lys | Arg<br>195 | Gly | Lys | Ala | Lys | Arg<br>200 | Gly | Cys | Ser | Pro | Arg<br>205 | Val | Lys | Pro |
| Gln | His<br>210 | Ile | Ser | Thr | His | Phe<br>215 | Leu | Pro | Arg | Phe | Lys<br>220 | Gln | Ser | Glu | Gln |
| Pro<br>225 | Glu | Leu | Ser | Phe | Thr<br>230 | Val | Thr | Val | Pro | Glu<br>235 | Lys | Lys | Asn | Pro | Pro<br>240 |
| Ser | Pro | Ile | Lys | Ser<br>245 | Lys | Ile | Pro | Leu | Ser<br>250 | Ala | Pro | Arg | Lys | Asn<br>255 | Thr |
| Asn | Ser | Val | Lys | Tyr<br>260 | Arg | Leu | Lys | Phe | Arg<br>265 | Phe | Gly |     |     |     |     |

260 265

(2) INFORMATION FOR SEQ ID NO:13:

(i) SEQUENCE CHARACTERISTICS:
        (A) LENGTH: 208 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:13:

```
Met Ala Pro Leu Gly Glu Val Gly Asn Tyr Phe Gly Val Gln Asp Ala
 1               5                  10                  15
Val Pro Phe Gly Asn Val Pro Val Leu Pro Val Asp Ser Pro Val Leu
                20                  25                  30
Leu Ser Asp His Leu Gly Gln Ser Glu Ala Gly Gly Leu Pro Arg Gly
            35                  40                  45
Pro Ala Val Thr Asp Leu Asp His Leu Lys Gly Ile Leu Arg Arg Arg
        50                  55                  60
Gln Leu Tyr Cys Arg Thr Gly Phe His Leu Glu Ile Phe Pro Asn Gly
65                  70                  75                  80
Thr Ile Gln Gly Thr Arg Lys Asp His Ser Arg Phe Gly Ile Leu Glu
                85                  90                  95
Phe Ile Ser Ile Ala Val Gly Leu Val Ser Ile Arg Gly Val Asp Ser
               100                 105                 110
Gly Leu Tyr Leu Gly Met Asn Glu Lys Gly Glu Leu Tyr Gly Ser Glu
               115                 120                 125
Lys Leu Thr Gln Glu Cys Val Phe Arg Glu Gln Phe Glu Glu Asn Trp
           130                 135                 140
Tyr Asn Thr Tyr Ser Ser Asn Leu Tyr Lys His Val Asp Thr Gly Arg
145                 150                 155                 160
Arg Tyr Tyr Val Ala Leu Asn Lys Asp Gly Thr Pro Arg Glu Gly Thr
                165                 170                 175
Arg Thr Lys Arg His Gln Lys Phe Thr His Phe Leu Pro Arg Pro Val
            180                 185                 190
Asp Pro Asp Lys Val Pro Glu Leu Tyr Lys Asp Ile Leu Ser Gln Ser
        195                 200                 205
```

(2) INFORMATION FOR SEQ ID NO:14:

(i) SEQUENCE CHARACTERISTICS:
        (A) LENGTH: 239 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:14:

```
Met Gly Leu Ile Trp Leu Leu Leu Leu Ser Leu Leu Glu Pro Gly Trp
 1               5                  10                  15
Pro Ala Ala Gly Pro Gly Ala Arg Leu Arg Arg Asp Ala Gly Gly Arg
                20                  25                  30
Gly Gly Val Tyr Glu His Leu Gly Gly Ala Pro Arg Arg Arg Lys Leu
            35                  40                  45
Tyr Cys Ala Thr Lys Tyr His Leu Gln Leu His Pro Ser Gly Arg Val
        50                  55                  60
Asn Gly Ser Leu Glu Asn Ser Ala Tyr Ser Ile Leu Glu Ile Thr Ala
```

```
              65                      70                       75                       80
Val   Glu   Val   Gly   Ile   Val   Ala   Ile   Arg   Gly   Leu   Phe   Ser   Gly   Arg   Tyr
                        85                      90                       95

Leu   Ala   Met   Asn   Lys   Arg   Gly   Arg   Leu   Tyr   Ala   Ser   Glu   His   Tyr   Ser
                  100                     105                      110

Ala   Glu   Cys   Glu   Phe   Val   Glu   Arg   Ile   His   Glu   Leu   Gly   Tyr   Asn   Thr
                  115                     120                      125

Tyr   Ala   Ser   Arg   Leu   Tyr   Arg   Thr   Val   Ser   Ser   Thr   Pro   Gly   Ala   Arg
      130                     135                      140

Arg   Gln   Pro   Ser   Ala   Glu   Arg   Leu   Trp   Tyr   Val   Ser   Val   Asn   Gly   Lys
145                           150                      155                            160

Gly   Arg   Pro   Arg   Arg   Gly   Phe   Lys   Thr   Arg   Arg   Thr   Gln   Lys   Ser   Ser
                        165                     170                      175

Leu   Phe   Leu   Pro   Arg   Val   Leu   Asp   His   Arg   Asp   His   Glu   Met   Val   Arg
                  180                     185                      190

Gln   Leu   Gln   Ser   Gly   Leu   Pro   Arg   Pro   Pro   Gly   Lys   Gly   Val   Gln   Pro
            195                     200                      205

Arg   Arg   Arg   Arg   Gln   Lys   Gln   Ser   Pro   Asp   Asn   Leu   Glu   Pro   Ser   His
      210                     215                      220

Val   Gln   Ala   Ser   Arg   Leu   Gly   Ser   Gln   Leu   Glu   Ala   Ser   Ala   His
225                           230                      235
```

( 2 ) INFORMATION FOR SEQ ID NO:15:

( i ) SEQUENCE CHARACTERISTICS:
        ( A ) LENGTH: 194 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:15:

```
Met   His   Lys   Trp   Ile   Leu   Thr   Trp   Ile   Leu   Pro   Thr   Leu   Leu   Tyr   Arg
1                       5                       10                       15

Ser   Cys   Phe   His   Ile   Ile   Cys   Leu   Val   Gly   Thr   Ile   Ser   Leu   Ala   Cys
                  20                      25                       30

Asn   Asp   Met   Thr   Pro   Glu   Gln   Met   Ala   Thr   Asn   Val   Asn   Cys   Ser   Ser
                  35                      40                       45

Pro   Glu   Arg   His   Thr   Arg   Ser   Tyr   Asp   Tyr   Met   Glu   Gly   Gly   Asp   Ile
            50                      55                       60

Arg   Val   Arg   Arg   Leu   Phe   Cys   Arg   Thr   Gln   Trp   Tyr   Leu   Arg   Ile   Asp
65                            70                      75                             80

Lys   Arg   Gly   Lys   Val   Lys   Gly   Thr   Gln   Glu   Met   Lys   Asn   Asn   Tyr   Asn
                        85                      90                       95

Ile   Met   Glu   Ile   Arg   Thr   Val   Ala   Val   Gly   Ile   Val   Ala   Ile   Lys   Gly
                  100                     105                      110

Val   Glu   Ser   Glu   Phe   Tyr   Leu   Ala   Met   Asn   Lys   Glu   Gly   Lys   Leu   Tyr
            115                     120                      125

Ala   Lys   Lys   Glu   Cys   Asn   Glu   Asp   Cys   Asn   Phe   Lys   Glu   Leu   Ile   Leu
      130                     135                      140

Glu   Asn   His   Tyr   Asn   Thr   Tyr   Ala   Ser   Ala   Lys   Trp   Thr   His   Asn   Gly
145                           150                      155                            160

Gly   Glu   Met   Phe   Val   Ala   Leu   Asn   Gln   Lys   Gly   Ile   Pro   Val   Arg   Gly
                        165                     170                      175
```

| Lys | Lys | Thr | Lys | Lys | Glu | Gln | Lys | Thr | Ala | His | Phe | Leu | Pro | Met | Ala |
|-----|-----|-----|-----|-----|-----|-----|-----|-----|-----|-----|-----|-----|-----|-----|-----|
|     |     |     | 180 |     |     |     |     | 185 |     |     |     |     | 190 |     |     |
| Ile | Thr |     |     |     |     |     |     |     |     |     |     |     |     |     |     |

NUCLEIC ACIDS AND CELLS FOR RECOMBINANT PRODUCTION OF FIBROBLAST GROWTH FACTOR-10

This invention relates to newly identified polynucleotides, polypeptides encoded by such polynucleotides, the use of such polynucleotides and polypeptides, as well as the production of such polynucleotides and polypeptides. More particularly, the polypeptide of the present invention is fibroblast growth factor-10/ heparin binding growth factor-10 (FGF-10). The invention also relates to inhibiting the action of such polypeptide.

Fibroblast growth factors are a family of proteins characteristic of binding to heparin and are, therefore, also called heparin binding growth factor (HBGF). Expression of different members of these proteins are found in various tissues and are under particular temporal and spatial control. These proteins are potent mitogens for a variety of cells of mesodermal, ectodermal, and endodermal origin, including fibroblasts, corneal and vascular endothelial cells, granulocytes, adrenal cortical cells, chondrocytes, myoblasts, vascular smooth muscle cells, lens epithelial cells, melanocytes, keratinocytes, oligodendrocytes, astrocytes, osteoblasts, and hematopoietic cells. Each member has functions overlapping with others and also has its unique spectrum of functions. In addition to the ability to stimulate proliferation of vascular endothelial cells, both FGF-1 & 2 are chemotactic for endothelial cells and FGF-2 has been shown to enable endothelial cells to penetrate the basement membrane. Consistent with these properties, both FGF-1 & 2 have the capacity to stimulate angiogenesis. Another important feature of these growth factors are their ability to promote wound healing. Many other members of the FGF family share similar activities with FGF-1 & 2 on promoting angiogenesis and wound healing. Several members of FGF gene family have been shown to induce mesoderm formation and to modulate differentiation of neuronal cells, adipocytes and skeletal muscle cells. Other than these biological activities in normal tissues, FGF proteins have been implicated in promoting tumoriogenesis in carcinomas and sarcomas by promoting tumor vascularization and as transforming proteins when the expression is deregulated.

Growth factors, especially heparin-binding and fibroblast growth factors, have recently been the subject of intensive study. The FGF family presently consists of eight structurally-related polypeptides. The genes for each have been cloned in sequence. Two of the members, FGF-1 and FGF-2, have been characterized under many names, but most often as acidic and basic fibroblast growth factor, respectively. The normal gene products influence the general proliferation capacity of the majority of mesoderm and neuroectoderm-derived cells. They are capable of inducing angiogenesis in vivo and may play important roles in early development. Burgess, W. H. and Maciag, T., Annu. Rev. Biochem., 58:575–606, (1989).

An eukaryotic expression vector encoding a secreted form of FGF-1 has been introduced by gene transfer into porcine arteries. This model defines gene function in the arterial wall in vivo. FGF-1 expression induced intimal thickening in porcine arteries 21 days after gene transfer. Nabel, E. G., et al., Nature, 362:844–6 (1993). It has further been demonstrated that basic fibroblast growth factor may regulate glioma growth and progression independent of its role in tumor angiogenesis and that basic fibroblast growth factor release or secretion may be required for these actions. Morrison, R. S., et al., J. Neurosci. Res., 34:502–9 (1993).

Fibroblast growth factors, such as basic FGF, have further been implicated in the growth of Kaposi's sarcoma cells in vitro. Huang, Y. Q., et al., J. Clin. Invest., 91:1191–7 (1993). Also, the cDNA sequence encoding for human basic fibroblast growth factor has been cloned downstream of a transcription promoter recognized by the bacteriophage T7 RNA polymerase. Basic fibroblast growth factors so obtained have been shown to have biological activity indistinguishable from human placental fibroblast growth factor in mitogenicity, synthesis of plasminogen activator and angiogenesis assays. Squires, C. H., et al., J. Biol. Chem., 263:16297–302 (1988).

U.S. Pat. No. 5,155,214 discloses substantially pure mammalian basic fibroblast growth factors and their production. The amino acid sequences of bovine and human basic fibroblast growth factor are disclosed, as well as the DNA sequence encoding the polypeptide of the bovine species.

In accordance with one aspect of the present invention, there is provided a novel mature polypeptide which is FGF-10, as well as fragments, analogs and derivatives thereof. The fibroblast growth factor (FGF) of the present invention is of human origin.

In accordance with another aspect of the present invention, there are provided polynucleotides (DNA or RNA) which encode such polypeptides.

In accordance with still another aspect of the present invention, there is provided a procedure for producing such polypeptide by recombinant techniques.

In accordance with yet a further aspect of the present invention, there is provided a process for utilizing such polypeptide, or polynucleotide encoding such polypeptide, for therapeutic purposes, for example, promoting healing due to wounds, burns and ulcers, and to prevent neuronal damage due to neuronal disorders, skin aging and hair loss.

In accordance with yet a further aspect of the present invention, there is provided an antibody against such polypeptide.

In accordance with yet another aspect of the present invention, there are provided antagonist/inhibitors to such polypeptides, which may be used to inhibit the action of such polypeptide, for example, in the treatment of tumors and hyper-vascular diseases.

These and other aspects of the present invention should be apparent to those skilled in the art from the teachings herein.

The following drawings are meant only as illustrations of specific embodiments of the present invention and are not meant as limitations in any manner.

FIGS. 1A–1C depict the cDNA sequence and corresponding deduced amino acid sequence of FGF-10. The amino acid sequence shown represents the mature form of the protein. The standard one letter abbreviation for amino acids is used.

FIGS. 2A–2D illustrate the homology between FGF-10 and the other FGF family members (SEQ ID NO:8–15)

Figure 3:
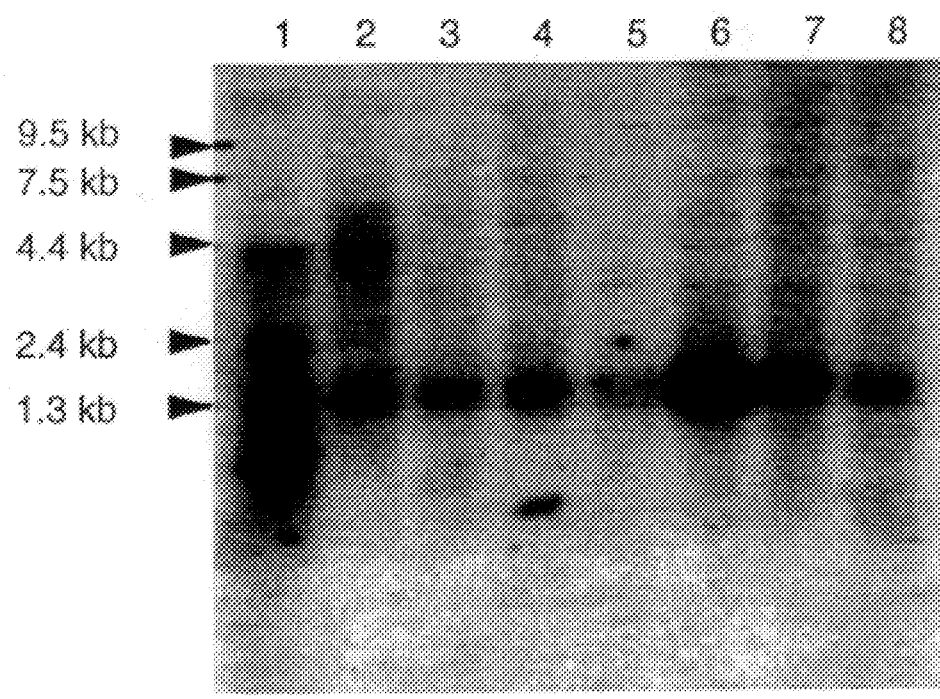
FIG. 3 depicts the results of a Northern blot analysis indicating the presence of the mRNA transcript for FGF-10 in human adult tissues.

In accordance with one aspect of the present invention, there is provided an isolated nucleic acid (polynucleotide) which encodes for the mature polypeptide having the deduced amino acid sequence of FIG. 1 (SEQ ID NO:2) or for the mature polypeptide encoded by the cDNA of the clone deposited as ATCC Deposit No. 75696 on Mar. 4, 1994.

The polynucleotide of this invention was discovered initially in a cDNA library derived from 8 week old early stage human tissue and subsequently the full length cDNA was found in a library derived from the human Amygdala. It is structurally related to all members of the fibroblast growth factor gene family and contains an open reading frame encoding a polypeptide of 239 amino acids. Among the top matches are: 1) 37% identity and 67% sequence similarity to FGF-9 isolated from brain over a stretch of 129 amino acids; 2) 36% identity and 64% similarity with FGF-7 (keratinocyte growth factor) in a region of 121 amino acids; 3) 33% identity and 55% similarity with FGF-1 (acidic FGF) over a stretch of 110 amino acids. Furthermore, the FGF/HBGF family signature, GXLX(S,T,A,G)X6(D,E)CXFXE (SEQ ID NO:3 is conserved in the gene of present invention, (X means any amino acid residue; (D,E) means either D or E residue; X6 means any 6 amino acid residue).

The polynucleotide of the present invention may be in the form of RNA or in the form of DNA, which DNA includes cDNA, genomic DNA, and synthetic DNA. The DNA may be double-stranded or single-stranded. The coding sequence which encodes the mature polypeptide may be identical to the coding sequence shown in FIGS. 1A–1C (SEQ ID NO:1) or that of the deposited clone or may be a different coding sequence, as a result of the redundancy or degeneracy of the genetic code, encodes the same, mature polypeptide as the DNA of FIGS. 1A–1C (SEQ ID NO:1) or the deposited cDNA.

The polynucleotide which encodes for the mature polypeptide of FIGS. 1A–1C (SEQ ID NO:2) or for the mature polypeptide encoded by the deposited cDNA may include: only the coding sequence for the mature polypeptide; the coding sequence for the mature polypeptide and additional coding sequence such as a leader or secretory sequence or a proprotein sequence; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of FIGS. 1A–1C (SEQ ID NO:2) or the polypeptide encoded by the cDNA of the deposited clone. The variant of the polynucleotide may be a naturally occurring allelic variant of the polynucleotide or a non-naturally occurring variant of the polynucleotide.

Thus, the present invention includes polynucleotides encoding the same mature polypeptide as shown in FIGS. 1A–1C (SEQ ID NO:2) or the same mature polypeptide encoded by the cDNA of the deposited clone as well as variants of such polynucleotides which variants encode for a fragment, derivative or analog of the polypeptide of FIGS. 1A–1C (SEQ ID NO:2) or the polypeptide encoded by the cDNA of the deposited clone. Such nucleotide variants include deletion variants, substitution variants and addition or insertion variants.

As hereinabove indicated, the polynucleotide may have a coding sequence which is a naturally occurring allelic variant of the coding sequence shown in FIGS. 1A–1C (SEQ ID NO:1) or of the coding sequence of the deposited clone. As known in the art, an allelic variant is an alternate form of a polynucleotide sequence which may have a substitution, deletion or addition of one or more nucleotides, which does not substantially alter the function of the encoded polypeptide.

The present invention also includes polynucleotides, wherein the coding sequence for the mature polypeptide may be fused in the same reading frame to a polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the mature form of the polypeptide. The polynucleotides may also encode for a proprotein which is the mature protein plus additional 5' amino acid residues. A mature protein having a prosequence is a proprotein and is an inactive form of the protein. Once the prosequence is cleaved an active mature protein remains.

Thus, for example, the polynucleotide of the present invention may encode for a mature protein, or for a protein having a prosequence or for a protein having both a prosequence and a presequence (leader sequence).

The polynucleotides of the present invention may also have the coding sequence fused in frame to a marker sequence which allows for purification of the polypeptide of the present invention. The marker sequence may be a hexa-histidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The present invention further relates to polynucleotides which hybridize to the hereinabove-described sequences if there is at least 50% and preferably 70% identity between the sequences. The present invention particularly relates to polynucleotides which hybridize under stringent conditions to the hereinabove-described polynucleotides . As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which retain substantially the same biological function or activity as the mature polypeptide encoded by the cDNA of FIGS. 1A–1C or the deposited cDNA.

The deposit(s) referred to herein will be maintained under the Budapest Treaty on the International Recognition of the Deposit of Microorganisms for the purposes of Patent Procedure. These deposits are provided merely as a convenience and are not an admission that a deposit is required under 35 U.S.C. §112. The sequence of the polynucleotides contained in the deposited materials, as well as the amino acid sequence of the polypeptides encoded thereby, are controlling in the event of any conflict with the description of sequences herein. A license may be required to make, use or sell the deposited materials, and no such license is hereby granted.

The present invention further relates to an FGF-10 polypeptide which has the deduced amino acid sequence of FIGS. 1A–1C (SEQ ID NO:2) or which has the amino acid sequence encoded by the deposited cDNA, as well as fragments, analogs and derivatives of such polypeptide.

The terms "fragment," "derivative" and "analog" when referring to the polypeptide of FIGS. 1A–1C (SEQ ID NO:2)

or that encoded by the deposited cDNA, means a polypeptide which retains essentially the same biological function or activity as such polypeptide. Thus, an analog includes a proprotein which can be activated by cleavage of the proprotein portion to produce an active mature polypeptide.

The polypeptide of the present invention may be a recombinant polypeptide, a natural polypeptide or a synthetic polypeptide, preferably a recombinant polypeptide.

The fragment, derivative or analog of the polypeptide of FIGS. 1A–1C (SEQ ID NO:2) or that encoded by the deposited cDNA may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or DNA or polypeptide, separated from some or all of the coexisting materials in the natural system, is isolated. Such polynucleotide could be part of a vector and/or such polynucleotide or polypeptide could be part of a composition, and still be isolated in that such vector or composition is not part of its natural environment.

The present invention also relates to vectors which include polynucleotides of the present invention, host cells which are genetically engineered with vectors of the invention and the production of polypeptides of the invention by recombinant techniques.

Host cells may be genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the FGF-10 genes. The culture conditions, such as temperature, pH and the like, are those previously used with the host cell selected for expression, and will be apparent to the ordinarily skilled artisan.

The polynucleotide of the present invention may be employed for producing a polypeptide by recombinant techniques. Thus, for example, the polynucleotide sequence may be included in any one of a variety of expression vehicles, in particular vectors or plasmids for expressing a polypeptide. Such vectors include chromosomal, nonchromosomal and synthetic DNA sequences, e.g., derivatives of SV40; bacterial plasmids; phage DNA; yeast plasmids; vectors derived from combinations of plasmids and phage DNA, viral DNA such as vaccinia, adenovirus, fowl pox virus, and pseudorabies. However, any other vector or plasmid may be used as long as they are replicable and viable in the host.

The appropriate DNA sequence may be inserted into the vector by a variety of procedures. In general, the DNA sequence is inserted into an appropriate restriction endonuclease sites by procedures known in the art. Such procedures and others are deemed to be within the scope of those skilled in the art.

The DNA sequence in the expression vector is operatively linked to an appropriate expression control sequence (s) (promoter) to direct mRNA synthesis. As representative examples of such promoters, there may be mentioned: LTR or SV40 promoter, the $E.$ $coli.$ lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain a gene to provide a phenotypic trait for selection of transformed host cells such as dihydrofolate reductase or neomycin resistance for eukaryotic cell culture, or such as tetracycline or ampicillin resistance in $E.$ $coli.$ The vector containing the appropriate DNA sequence as herein above described, as well as an appropriate promoter or control sequence, may be employed to transform an appropriate host to permit the host to express the protein. As representative examples of appropriate hosts, there may be mentioned: bacterial cells, such as $E.$ $coli$ , Salmonella typhimurium, Streptomyces; fungal cells, such as yeast; insect cells, such as Drosophila and Sf9; animal cells such as CHO, COS or Bowes melanoma; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen), pBs, phagescript, psiX174, pBluescript SK, pBsKS, pNH8a, pNH16a, pNH18a, pNH46a (Stratagene); pTrc99A, pKK223-3, pKK233-3, pDR540, pRIT5 (Pharmacia). Eukaryotic: pWLneo, pSV2cat, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described construct. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, 1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook. et al., Molecular Cloning: A Laboratory Manual, Second Edition, (Cold Spring Harbor, N.Y., 1989), the disclosure of which is hereby incorporated by reference.

Transcription of a DNA encoding the polypeptides of the present invention is increased by higher eukaryotes by inserting an enhancer sequence into the vector. Enhancers are cis-acting elements of DNA, usually about from 10 to 300 bp, that act on a promoter to increase its transcription. Examples include the SV40 enhancer on the late side of the replication origin (bp 100 to 270), a cytomegalovirus early promoter enhancer, a polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), α factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli*, *Bacillus subtilis*, *Salmonella typhimurium* and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These PBR322 "backbone" sections are combined with an appropriate promoter and the structural sequence to be expressed.

Following transformation of a suitable host strain and growth of the host strain to an appropriate cell density, the selected promoter is derepressed by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 viral genome, for example, SV40 origin, early promoter, enhancer, splice, and polyadenylation sites may be used to provide the required nontranscribed genetic elements.

FGF-10 may be recovered and purified from recombinant cell cultures by methods used heretofore, including ammonium sulfate or ethanol precipitation, acid extraction, anion or cation exchange chromatography, phosphocellulose chromatography, hydrophobic interaction chromatography, affinity chromatography, hydroxyapatite chromatography and lectin chromatography. It is preferred to have low concentrations (approximately 0.1–5 mM) of calcium ion present during purification (Price, et al., J. Biol. Chem., 244:917 (1969)). Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated with mammalian or other eukaryotic carbohydrates or may be non-glycosylated. Polypeptides of the invention may also include an initial methionine amino acid residue.

The polypeptide of the present invention can be used in treatment for stimulating revascularization of ischemic tissues due to various disease conditions such as thrombosis, arteriosclerosis, and other cardiovascular conditions, since many FGFs stimulate vascular endothelial cell growth.

FGF may also be used for treating wounds due to injuries, burns, post-operative tissue repair, and ulcers since many known FGFs have the ability to be a mitogenic agent to various cell types, such as fibroblast cells and skeletal muscle cells.

FGF-10 may also be used to treat and prevent neuronal damage which occurs in certain neuronal disorders or neurodegenerative conditions such as Alzheimer's disease, Parkinson's disease, and AIDS-related complex. Since many FGFs also have the ability to stimulate chondrocyte growth, it may be used to enhance bone and periodontal regeneration and aid in tissue transplants or bone grafts. Another potential use for FGF-10 is to prevent skin aging due to sunburn, since some FGFs stimulate keratinocyte growth.

FGF-10 may also be useful for preventing hair loss, since some FGFs activate hair-forming cells and promote melanocyte growth. Along the same lines, FGFs stimulate growth and differentiation of hematopoietic cells and bone marrow cells when used in combination with other cytokines.

FGF-10 may also be used to maintain organs before transplantation or for supporting cell culture of primary tissues. FGF-10 can further be used to identify new receptors for FGF, such that new therapeutic uses of FGF-10 may be identified by such action.

The polypeptide of the present invention may also be employed in accordance with the present invention by expression of such polypeptide in vivo, which is often referred to as "gene therapy."

Thus, for example, cells may be engineered with a polynucleotide (DNA or RNA) encoding for the polypeptide ex vivo, the engineered cells are then provided to a patient to be treated with the polypeptide. Such methods are well-known in the art. For example, cells may be engineered by procedures known in the art by use of a retroviral particle containing RNA encoding for the polypeptide of the present invention.

Similarly, cells may be engineered in vivo for expression of the polypeptide in vivo, for example, by procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such methods should be apparent to those skilled in the art from the teachings of the present invention. For example, the expression vehicle for engineering cells may be other than a retroviral particle, for example, an adenovirus, which may be used to engineer cells in vivo after combination with a suitable delivery vehicle.

The polypeptides of the present invention may be employed in combination with a suitable pharmaceutical carrier. Such compositions comprise a therapeutically effective amount of the protein, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptide of the present invention may be employed in conjunction with other therapeutic compounds.

The pharmaceutical compositions may be administered in a convenient manner, such as the oral, intravenous, intraperitoneal, intramuscular, subcutaneous, intranasal or intradermal routes, although topical application is preferred. The amounts and dosage regimens of FGF-10 administered to a subject will depend on a number of factors, such as the mode of administration, the nature of the condition being treated, the body weight of the subject being treated, and the judgment of the prescribing physician. Generally speaking, it is given in therapeutically effective doses of at least about 10 μg/kg body weight and in most cases it would be administered in an amount not in excess of about 8 mg/kg body weight per day and preferably the dosage is from about 10 μg/kg body weight to about 1 mg/kg body weight daily, taking into account the routes of administration, symptoms, etc.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphism's) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the cDNA is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA as short as 500 or 600 bases; however, clones larger than 2,000 bp have a higher likelihood of binding to a unique chromosomal location with sufficient signal intensity for simple detection. FISH requires use of the clone from which the EST was derived, and the longer the better. For example, 2,000 bp is good, 4,000 is better, and more than 4,000 is probably not necessary to get good results a reasonable percentage of the time. For a review of this technique, see Verma et al., Human Chromosomes: a Manual of Basic Techniques. Pergamon Press, New York (1988).

Once a sequence has been mapped to a precise chromosomal location, the physical position of the sequence on the chromosome can be correlated with genetic map data. (Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

Comparison of affected and unaffected individuals generally involves first looking for structural alterations in the chromosomes, such as deletions or translocations that are visible from chromosome spreads or detectable using PCR based on that cDNA sequence. Ultimately, complete sequencing of genes from several individuals is required to confirm the presence of a mutation and to distinguish mutations from polymorphisms.

The present invention is further directed to inhibiting FGF-10 in vivo by use of antisense technology. Antisense technology can be used to control gene expression through triple-helix formation or antisense DNA or RNA, both of which methods are based on binding of a polynucleotide sequence to DNA or RNA. For example, the 5' coding portion of the polynucleotide sequence, which encodes for the mature polypeptide of the present invention, is used to design an antisense RNA oligonucleotide of from 10 to 40 base pairs in length. A DNA oligonucleotide is designed to be complementary to a region of the gene involved in transcription (triple helix—see Lee et al, Nucl. Acids Res., 6:3073 (1979); Cooney et al, Science, 241:456 (1988); and Dervan et al, Science, 251:1360 (1991), thereby preventing transcription and the production of FGF-10. The antisense RNA oligonucleotide hybridizes to the mRNA in vivo and blocks translation of an mRNA molecule into the FGF-10 polypeptide (antisense—Okano, J. Neurochem., 56:560 (1991); Oligodeoxynucleotides as Antisense Inhibitors of Gene Expression, CRC Press, Boca Raton, Fla. (1988)). Alternatively, the oligonucleotides described above can be delivered to cells by procedures in the art such that the anti-sense RNA or DNA may be expressed in vivo to inhibit production of FGF-10 in the manner described above.

Antisense constructs to FGF-10, therefore, inhibit the stimulation of cell growth by FGF-10 and prevent further growth or even regress tumors, hyper-vascular diseases, and cause the proliferation of epithelial lens cells after extracapsular cataract surgery.

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain and humanized antibodies, as well as Fab fragments, or the product of a Fab expression library. Various procedures known in the art may be used for the production of such antibodies and fragments.

Antibodies generated against the polypeptide corresponding to a sequence of the present invention can be obtained by direct injection of the polypeptide into an animal or by administering the polypeptide to an animal, preferably a nonhuman. The antibody so obtained will then bind the polypeptide itself. In this manner, even a sequence encoding only a fragment of the polypeptide can be used to generate antibodies binding the whole native polypeptide. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, Nature, 256:495–497 (1975)), the trioma technique, the human B-cell hybridoma technique (Kozbor et al., Immunology Today 4:72 (1983)), and the EBV-hybridoma technique to produce human monoclonal antibodies (Cole, et al., Monoclonal Antibodies and Cancer Therapy, Alan R. Liss, Inc., pp. 77–96 (1985)).

Techniques described for the production of single chain antibodies (U.S. Pat. No. 4,946,778) can be adapted to produce single chain antibodies to immunogenic polypeptide products of this invention.

Antibodies specific to FGF-10 that can bind to and inactivate the protein may be used to inhibit the cell growth and proliferation effect of FGF-10 and therefore retard or prevent the growth of tumors. These antibodies may also be used to prevent hyper-vascular diseases, and help the proliferation of epithelial lens cells after extracapsular cataract surgery.

The present invention is also directed to antagonist/inhibitors of the polypeptides of the present invention. The antagonist/inhibitors are those which inhibit or eliminate the function of the polypeptide.

Thus, for example, antagonists can bind to a polypeptide of the present invention and inhibit or eliminate its function. The antagonist, for example, could be an antibody against the polypeptide or, in some cases, an oligonucleotide. An example of an inhibitor is a small molecule which binds to the catalytic site of the polypeptide making it inaccessible to substrate and preventing biological activity. Examples of small molecule inhibitors include but are not limited to small peptides or peptide-like molecules.

Alternatively, antagonists to the polypeptides of the present invention may be employed which bind to the receptors to which a polypeptide of the present invention normally binds. The antagonists may be closely related proteins such that they recognize and bind to the receptor sites of the natural protein, however, they are inactive forms of the natural protein and thereby prevent the action of FGF-10 since receptor sites are occupied. In these ways, the antagonist/inhibitors may be used therapeutically as an anti-tumor drug and may also be used to prevent hyper-vascular diseases or the proliferation of epithelial lens cells after extra-capsular cataract surgery.

The antagonist/inhibitors may be employed in a composition with a pharmaceutically acceptable carrier, e.g., as hereinabove described.

The present invention will be further described with reference to the following examples; however, it is to be understood that the present invention is not limited to such examples. All parts or amounts, unless otherwise specified, are by weight.

In order to facilitate understanding of the following examples, certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 $\mu$g of plasmid or DNA fragment is used with about 2 units of enzyme in about 20 $\mu$l of buffer solution. For the purpose of isolating DNA fragments for plasmid construction, typically 5 to 50 $\mu$g of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units of T4 DNA ligase ("ligase") per 0.5 μg of approximately equimolar amounts of the DNA fragments to be ligated.

Unless otherwise stated, transformation was performed as described by the method of Graham, F. and Van der Eb, A., Virology, 52:456–457 (1973).

EXAMPLE 1

Tissue Distribution of FGF-10 mRNA in Human Adult Tissues

To analyze the expression of FGF-10 mRNA, Northern analysis was performed with 2 μg of poly $A^+$ mRNA from several human adult tissues using radioactively labeled entire FGF-10 cDNA as a probe. The results indicate that a 1.4 kb message is expressed most abundantly in the skeletal muscle, at intermediate level in the heart, brain, placenta, kidney, and pancreas, and at lower level in the liver. In heart, 3 other fragments with sizes of 4.4 kb, 2.4 kb, and 0.5 kb are also present. It is likely that these different size of mRNA in heart result from alternative splicing. In brain, a 4.4 kb mRNA is also present. The nylon blot with 2 ug of poly A+ mRNA from several human adult tissues bound to the membrane was obtained from Clontech Laboratories, Inc. Palo Alto, Calif. The blot was hybridized with the entire FGF-10 cDNA labeled with radioactive dCTP by random-primed labeling. The hybridization was performed in 7% SDS, 0.5M NaPO4, pH 7.2, and 1% BSA at 65° C. overnight. Following 2x30 min wash in 0.2xSSC, 0.1% SDS at 65° C., the blot was exposed to X-ray film with intensifying screen overnight. See FIG. 3.

EXAMPLE 2

Expression of FGF-10 by In vitro Transcription and Translation

The FGF-10 cDNA was transcribed and translated in vitro to determine the size of the translatable polypeptide encoded by the full length and partial FGF-10 cDNA. The full length and partial cDNA inserts of FGF-10 in the pBluescript SK vector were amplified by PCR with three paris of primers, 1) M13-reverse and forward primers; 2) M13-reverse primer and FGF primer P20; 3) M13-reverse primer and FGF primer P22. The sequence of these primers as follows.

M13-2 reverse primer:

5'-ATGCTTCCGGCTCGTATG-3' (SEQ ID NO:4)

This sequence is located upstream of the 5' end of the FGF-10 cDNA insert in the pBluescript vector and is in an anti-sense orientation as the cDNA. A T3 promoter sequence is located between this primer and the FGF-10 cDNA.

M-13-2 forward primer:

5'-GGGTTTTCCCAGTCACGAC-3' (SEQ ID NO:5)

This sequence is located downstream of the 3' end of the FGF-10 cDNA insert in the pBluescript vector and is in an anti-sense orientation as the cDNA insert.

FGF primer P20:

5'-GTGAGATCTGAGGGAAGAAGGGGA-3' (SEQ ID NO:6)

The 15 bp sequence of this primer on the 3' prime is anti-sense to the FGF-10 cDNA sequence bp 780–766, which is 12 bp downstream from the stop codon.

FGF primer P22:

5'-CCACCGATAATCCTCCTT-3' (SEQ ID NO:7)

This sequence is located within the FGF-10 cDNA in an anti-sense orientation and is about 213 bp downstream from the stop codon.

PCR reaction with all three pairs of primers produce amplified products with T3 promoter sequence in front of the cDNA insert. All three pairs of primers produce PCR products that encode the full polypeptide of FGF-10.

Approximately 1 ug of PCR product from first pair of primers, 0.3 ug from second pair of primers, 0.3 ug from third pair of primers were used for in vitro transcription/translation. The in vitro transcription/translation reaction was performed in a 25 ul of volume, using the $T_NT$™ Coupled Reticulocyte Lysate Systems (Promega, CAT #L4950). Specifically, the reaction contains 12.5 ul of $T_NT$ rabbit reticulocyte lysate 2 ul of $T_NT$ reaction buffer, 1 ul of T3 polymerase, 1 ul of 1 mM amino acid mixture (minus methionine), 4 ul of $^{35}S$-methionine (>1000 Ci/mmol, 10 mCi/ml), 1 ul of 40 U/ul; RNasin ribonuclease inhibitor, 0.5 or 1 ug of PCR products. Nuclease-free $H_2O$ were added to bring the me to 25 ul. The reaction was incubated at 30° C. for 2 hours. Five microliters of the reaction product was analyzed on a 4–20% gradient SDS-PAGE gel. After fixing in 25% isopropanol and 10% acetic acid, the gel was dried and exposed to an X-ray film overnight at 70° C.

Figure 4:
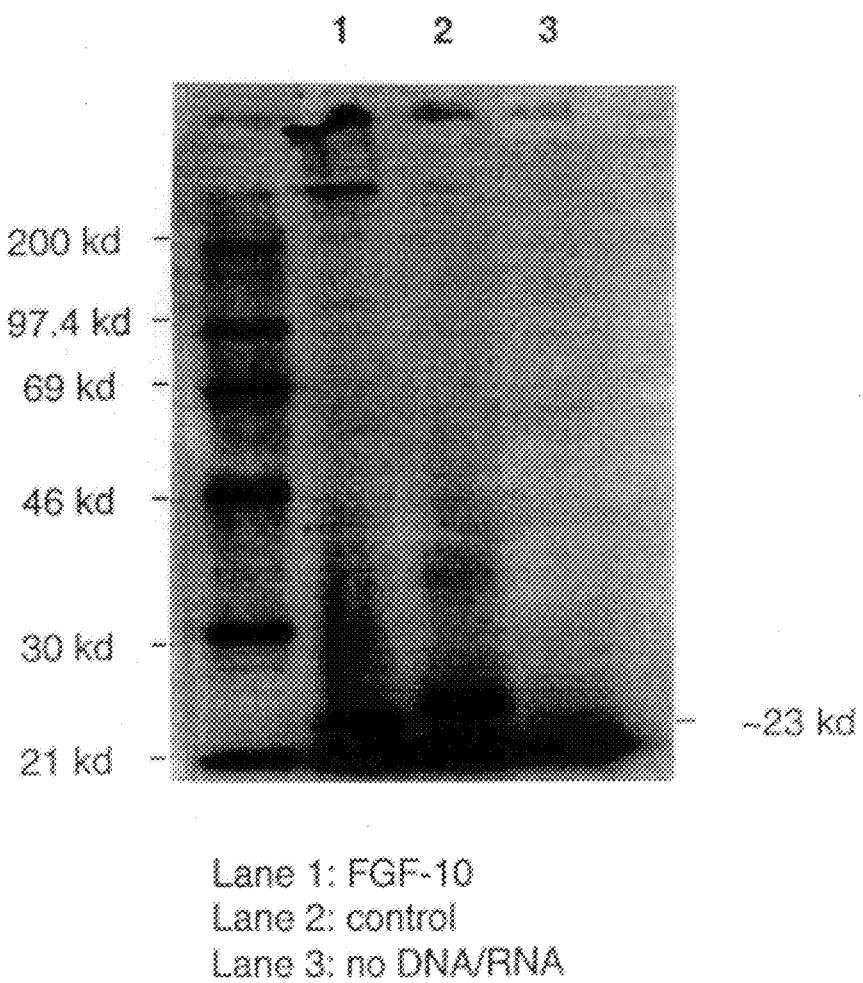
FIG. 4 shows an SDS-PAGE gel after in vitro transcription/translation of FGF-10 protein.

As shown in FIG. 4, PCR products containing the full length FGF-10 cDNA and the cDNA missing ~340 bp and ~140 bp in the 3' un-translated region (3'-UTR) produced the same length of translated products, whose molecular weights are estimated to be around 19 kd (lanes 1–3).

Numerous modifications and variations of the present invention are possible in light of the above teachings and, therefore, within the scope of the appended claims, the invention may be practiced otherwise than as particularly described.

What is claimed is:

1. An isolated polynucleotide comprising a polynucleotide having at least 95% identity to a member selected from the group consisting of:
   (a) a polynucleotide encoding a polypeptide comprising the amino acid sequence as set forth in SEQ ID NO:2; and
   (b) the complement of (a).

2. The isolated polynucleotide of claim 1 wherein said member is (a).

3. The isolated polynucleotide of claim 1 comprising a polynucleotide which has at least a 97% identity to said member.

4. The isolated polynucleotide of claim 1 comprising a polynucleotide encoding a polypeptide comprising amino acid 1 to amino acid 181 as set forth in SEQ ID NO:2.

5. The isolated polynucleotide of claim 4 comprising nucleotide 1 to nucleotide 1121 of SEQ ID NO:1.

6. The isolated polynucleotide of claim 4 comprising nucleotide 210 to nucleotide 752 of SEQ ID NO:1.

7. The isolated polynucleotide of claim 4 wherein the polynucleotide is DNA.

8. The isolated polynucleotide of claim 4 wherein the polynucleotide is RNA.

9. The polynucleotide of claim 4 wherein the polynucleotide is genomic DNA.

10. An isolated polynucleotide comprising a polynucleotide having at least 95% identity to a member selected from the group consisting of:
    (a) a polynucleotide encoding a polypeptide comprising amino acids 2 to 181 as set forth in SEQ ID NO:2; and
    (b) the complement of (a).

11. The isolated polynucleotide of claim 10 comprising a polynucleotide encoding a polypeptide comprising amino acids 2 to 181 of SEQ ID NO:2.

12. The isolated polynucleotide of claim 10 wherein said member is (a).

13. An isolated polynucleotide comprising a polynucleotide having at least 95% identity to a member selected from the group consisting of:
    (a) a polynucleotide encoding the polypeptide encoded by the human cDNA contained in ATCC Deposit No. 75696; and
    (b) the complement of (a).

14. The isolated polynucleotide of claim 13 wherein said member is (a).

15. The isolated polynucleotide of claim 13 comprising a polynucleotide encoding the polypeptide encoded by the human cDNA contained in ATCC Deposit No. 75696.

16. The isolated polynucleotide of claim 13 comprising the human cDNA contained in ATCC Deposit No. 75696 encoding polypeptide.

17. A process for making a recombinant vector comprising inserting the polynucleotide of claim 1 into a vector.

18. A process for making a recombinant vector comprising inserting the polynucleotide of claim 4 into a vector.

19. A process for making a recombinant vector comprising inserting the polynucleotide of claim 13 into a vector.

20. A process for making a recombinant vector comprising inserting the polynucleotide of claim 14 into a vector.

21. A vector comprising the polynucleotide of claim 2 wherein said polynucleotide is DNA.

22. A vector comprising the polynucleotide of claim 4 wherein said polynucleotide is DNA.

23. A vector comprising the polynucleotide of claim 5 wherein said polynucleotide is DNA.

24. A vector comprising the polynucleotide of claim 6 wherein said polynucleotide is DNA.

25. A vector comprising the polynucleotide of claim 14.

26. A vector comprising the polynucleotide of claim 15 wherein said polynucleotide is DNA.

27. A vector comprising the polynucleotide of claim 16.

28. A process for producing a modified cell comprising introducing into a cell the vector of claim 21.

29. A process for producing a modified cell comprising introducing into a cell the vector of claim 22.

30. A process for producing a modified cell comprising introducing into a cell the vector of claim 23.

31. A process for producing a modified cell comprising introducing into a cell the vector of claim 24.

32. A process for producing a modified cell comprising introducing into a cell the vector of claim 25.

33. A process for producing a modified cell comprising introducing into a cell the vector of claim 26.

34. A process for producing a modified cell comprising introducing into a cell the vector of claim 27.

35. A host cell comprising the vector of claim 21.

36. A host cell comprising the vector of claim 22.

37. A host cell comprising the vector of claim 23.

38. A host cell comprising the vector of claim 24.

39. A host cell comprising the vector of claim 25.

40. A host cell comprising the vector of claim 26.

41. A host cell comprising the vector of claim 27.

42. A process for producing a polypeptide, comprising:
    culturing a cell containing the polynucleotide of claim 2 in the form of DNA and encoding a polypeptide selected from the group consisting of:
    (a) a polypeptide comprising the amino acid sequence of SEQ ID NO:2, and
    (b) a polypeptide having mitogenic activity and comprising the amino acid sequence of SEQ ID NO:2 substituted with one or more conservative amino acid substitutions,
    said culturing being under conditions which express the polypeptide encoded by said polynucleotide.

43. A process for producing a polypeptide comprising:
    culturing a cell containing the polynucleotide of claim 4 in the form of DNA under conditions which express the polypeptide encoded by the polynucleotide.

44. A process for producing a polypeptide comprising:
    culturing a cell containing the polynucleotide of claim 5 in the form of DNA under conditions which express the polypeptide encoded by the polynucleotide.

45. A process for producing a polypeptide comprising:
    culturing a cell containing the polynucleotide of claim 6 in the form of DNA under conditions which express the polypeptide encoded by the polynucleotide.

46. A process for producing a polypeptide, comprising:
    culturing a cell containing the polynucleotide of claim 12 in the form of DNA and encoding a polypeptide selected from the group consisting of:

(a) a polypeptide comprising amino acids 2–181 of SEQ ID NO:2, and
(b) a polypeptide having mitogenic activity and comprising amino acids 2–181 of SEQ ID NO:2 substituted with one or more conservative amino acid substitutions, said culturing being under conditions which express the polypeptide encoded by said polynucleotide.

47. A process for producing a polypeptide, comprising:

culturing a cell containing the polynucleotide of claim 14 in the form of DNA and encoding a polypeptide selected from the group consisting of:
(a) a polypeptide comprising the polypeptide encoded by the human cDNA contained in ATCC Deposit No. 75696; and
(b) a polypeptide having mitogenic activity and comprising the polypeptide encoded by the human cDNA contained in ATCC Deposit No. 75696, substituted with one or more conservative amino acid substitutions, said culturing being under conditions which express the polypeptide encoded by said polynucleotide.

48. A process for producing a polypeptide comprising:

culturing a cell containing the polynucleotide of claim 15 in the form of DNA under conditions which express the polypeptide encoded by the polynucleotide.

49. A process for producing a polypeptide comprising:

culturing a cell containing the polynucleotide of claim 16 in the form of DNA under conditions which express the polypeptide encoded by the polynucleotide.

\* \* \* \* \*